United States Patent
Rubin

(12) 
(10) Patent No.: US 6,482,009 B1
(45) Date of Patent: Nov. 19, 2002

(54) ROOT CANAL TESTING IMPLEMENT AND METHOD

(76) Inventor: Gregory Rubin, 24704 Calle Conejo, Calabasas, CA (US) 91302

( * ) Notice: Subject to any disclaimer, the term of this patent is extended or adjusted under 35 U.S.C. 154(b) by 0 days.

(21) Appl. No.: 09/899,483

(22) Filed: Jul. 4, 2001

(51) Int. Cl.$^7$ ................................................. A61C 5/02
(52) U.S. Cl. ......................................... 433/224; 433/81
(58) Field of Search ................................... 433/224, 81

(56) References Cited

U.S. PATENT DOCUMENTS

| | | | | |
|---|---|---|---|---|
| 2,626,855 A | * | 1/1953 | Hand | 436/20 |
| 2,927,056 A | * | 3/1960 | Gurney | 433/224 |
| 3,961,530 A | * | 6/1976 | Helgesson | 374/162 |
| 5,725,373 A | * | 3/1998 | Yeh | 433/72 |
| 6,004,133 A | * | 12/1999 | Harrison, III | 433/224 |

* cited by examiner

Primary Examiner—John J. Wilson

(57) ABSTRACT

A method of and device for testing for conditions, particularly moisture conditions, in root canals and for drying the root canal. In accordance with the method, a small pointed implement in the nature of a rolled piece of paper having pH indicator on the tip thereof is inserted into the root canal. The pH indictor, by change of color, will present information as to whether or not any moisture is present in the canal and, secondly, whether or not the moisture is a positive pH or negative pH.

10 Claims, 1 Drawing Sheet

ROOT CANAL TESTING IMPLEMENT AND METHOD

BACKGROUND OF THE INVENTION

1. Field of the Invention

This invention relates in general to certain new and useful improvements in methods and devices for testing the condition of a tooth root canal and, more particularly, to a simple and easy test for determining whether there is moisture present in the root canal of a tooth and further whether the moisture, if any, is of a positive or a negative pH prior to sealing the root canal with a sealing material.

2. Brief Description of Related Art

Although the science relating to dental procedures has increased dramatically over the years, there remains some relatively simple but yet perplexing problems which still confront the dentist in the performing of and preparation of root canals. It is well established that a root canal must be perfectly dry and contain no presence of moisture whatsoever before any filling can be introduced into the root canal. In some cases, a dentist will attempt to use a small diameter cotton swab and attempt to wipe the wall of the canal with this cotton swab or use paper points, as hereinafter described.

The tooth canal is usually curved and, moreover, of a relatively small cross-sectional size. Consequently, a swab is not capable of being inserted to any reasonable depth within the root canal.

Many dentists will attempt to use air from an air jet supplied from a pressurized source of air. However, the air in this pressurized source frequently does contain a small amount of moisture and the moisture from that air can actually condense in the root canal of the tooth, thereby militating against the use of air.

There are presently devices known as paper points which are frequently used by dentists in an attempt to wipe the wall of the root canal, particularly at the lower depths thereof. In this case, paper, typically of a triangular shape, is rolled by a manufacturer of these paper points into small thin rod-like elements having a point at an end adapted for insertion into the canal of the tooth. In this case, the paper itself is somewhat moisture absorbent and tends to absorb some of the moisture which may be present in the root canal of the tooth. However, the drying of the canal with a paper point is frequently not sufficient. One of the more important problems arising from the use of these paper points is the fact that there is no effective and convenient means to determine whether or not moisture is still present in the tooth, even after the attempts to remove all moisture. As a result, some dentists will attempt to continue with the filling of the tooth, even though moisture could be present and this may further result in additional deterioration, if not infection, of the tooth and poor treatment prognosis.

In some cases, a dentist will attempt to take a paper point, insert the same into a root canal of a tooth, withdraw the paper point and attempt to bend the paper point on a dental tray or other surface. This rudimentary test is designed to determine if moisture is present which had been absorbed in the paper point causing the same to bend easily. Obviously, this is, at very best, a rudimentary test and certainly is not effective to determine if all moisture has effectively been removed.

Frequently, the dentist is unable to insert the swab to the lowest depth of the canal and this is the point at which water would tend to accumulate. Consequently, there is no effective and reliable means for insuring that all moisture has been removed from the canal before any further procedure takes place.

One of the problems associated with root canals is the presence of infection. When the pulp chamber of the tooth is opened, there is a tendency for bacterial growth to occur within the open cavity of the tooth. Frequently, until this bacterial growth has at least caused some damage or associated pain and discomfort, the bacteria remains undetected. Consequently, it is quite important for the dentist to be able to detect the presence of any bacterial condition which may exist in the root canal.

It would therefore be desirable to provide a device which is accurate and reliable and of low cost for determining whether moisture may be present in the root canal of a tooth. In addition, it would also be desirable to provide an inexpensive and effective means which could aid in determining bacterial presence and potentially as an aid to determining the general class of bacteria.

OBJECTS OF THE INVENTION

It is, therefore, one of the primary objects of the present invention to provide a method for insuring that all moisture in a root canal of a tooth has been removed.

It is another object of the present invention to provide a method for aiding in determining the presence of any infected body fluid in a root canal.

It is also an object of the present invention to provide a device for determining whether or not moisture is present in a root canal of a tooth by a simple visual color change test.

It is yet another salient object of the present invention to provide a device of the type stated which can be constructed at a relatively low unit cost and which is highly effective in operation and highly reliable in use.

With the above and other objects in view, my invention resides in the novel features of form, construction, arrangement, and combination of parts as presently described and pointed out in the claims.

BRIEF SUMMARY OF THE INVENTION

The present invention relates in general terms to a device and a method for testing whether or not moisture is present in a root canal of a tooth and for also drying the canal to insure removal of all moisture. Moreover, the present invention relates to the device and method which can be used as an aid for determining whether or not bacterial growth may be present in the root canal of a tooth.

The present invention relies upon a relatively small diameter implement, such as a paper point of the type frequently used by dentists. In this case, a pH indicator is impregnated into the lower portion or apocal region of the paper point in order to determine whether or not moisture is present in the root canal of the tooth. In place of a paper point, it is also possible to use a relatively small diameter implement, such as a very thin diameter implement, which is impregnated with a pH indicator at the lower end thereof. However, it is necessary for the device to be somewhat bendable in order to conform to the curvature of the root canal in many teeth.

By inserting a paper point or similar implement into the root canal of the tooth, if moisture is present, the pH indicator impregnated into the lower end of the paper point or other implement will be actuated by moisture and change colors. In this way, the dentist will be immediately advised of the presence of moisture by virtue of the color change.

If moisture is detected, the dentist can thereupon attempt to use some other means for drying out the root canal as, for example, additional paper points to absorb any remaining moisture in the root canal. Thereafter, the dentist or other technician can insert yet another paper point with a pH indicator on the lower end in order to determine if all moisture has been removed. The paper point will not change color if there is no other moisture present in the root canal.

In addition to the foregoing, it is sometimes necessary to determine whether or not infected body fluids may be present in a root canal. If the implement which is inserted in the root canal shows the presence of blood, then the dentist or technician is immediately advised of a certain condition which must be treated. Otherwise, if the pH indicator shows either a positive or negative pH, this will provide very basic information to the dentist or other dental practitioner as to possible types of bacterial growth which may be present. The use of pH indicating tests is not effective to actually determine a specific type of bacterial growth. However, indication as to whether or not the pH is positive or negative could provide some basis as to potential types of infection.

The present thereby provides both a method for detecting the presence of moisture and for aiding in detecting the presence of an infection or other tooth condition which requires treatment. The device in the nature of a pre-impregnated paper point can be produced at a very low unit cost and is highly reliable in its operation. In addition, the method of the invention can be performed with a minimum amount of manual attention and can also be performed very quickly.

This invention possesses many other advantages and has other purposes which may be made more clearly apparent from a consideration of the forms in which it may be embodied. These forms are shown in the drawings forming a part of and accompanying the present specification. They will now be described in detail for purposes of illustrating the general principles of the invention. However, it is to be understood that the following detailed description and the accompanying drawings are not to be taken in a limiting sense.

BRIEF DESCRIPTION OF THE DRAWINGS

Figure 1:
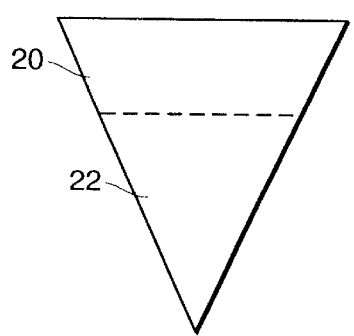
Figure 2:
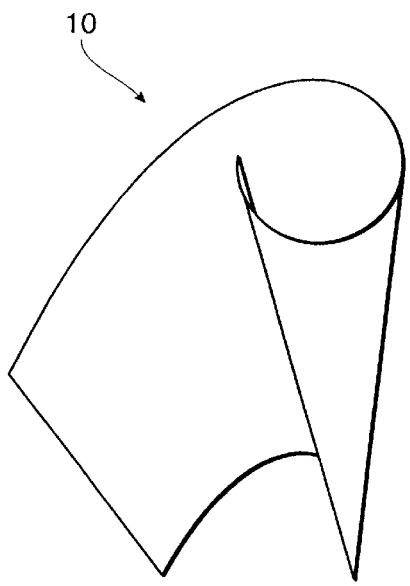
Figure 3:
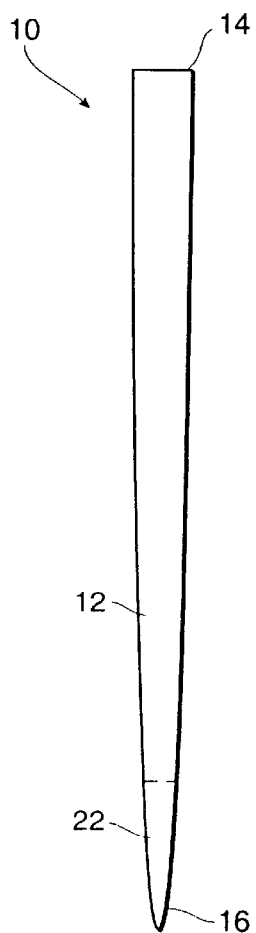
Figure 4:
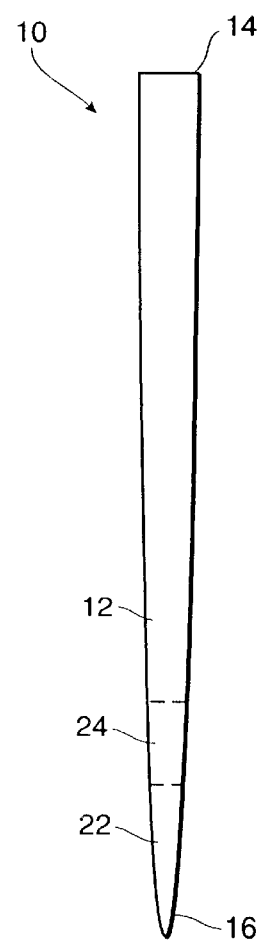

Having thus described the invention in general terms, reference will now be made to the accompanying drawings in which:

FIG. 1 is a plan view of a piece of absorbent paper in triangular shape which is used to make the paper point of the present invention;

FIG. 2 is a perspective view showing the piece of absorbent paper of FIG. 1 being rolled into a paper point;

FIG. 3 is a side elevational view of a paper point used in accordance with the present invention; and FIG. 4 is a side elevational view of a modified form of paper point which may be used in accordance with the present invention.

DETAILED DESCRIPTION OF A PREFERRED EMBODIMENT

Referring now in more detail and by reference characters to the drawings, FIG. 3 illustrates one device 10 which may be used for testing for the presence of moisture in a root canal of a tooth. The device 10 generally comprises an elongate paper point having a shank 12 and an enlarged upper end 14 for engagement by the hands of a user as well as a pointed lower end or tip 16 for insertion into a root canal.

The paper point of the invention is preferably formed from a piece of triangularly shaped absorbent paper 20, as shown in FIG. 1, and which is rolled into a paper point, such as the paper point 10 in the manner as initially shown in FIG. 2. The paper point of the invention is preferably pre-impregnated at its lower point or tip portion with a pH indicator region 22, as best shown in both FIGS. 1 and 3 of the drawings. In this case, the moisture testing device of the invention is therefore formed of a rolled paper material but which is still sufficiently durable to be inserted into a canal of a tooth. Inasmuch as the device is a throw away device, that is, after it has been used on one occasion, it is disposable, any light weight and even relatively degradable material can be used for this purpose. It is important to be able to ensure that a pH indicator can be applied to the lower end of the shank 12.

By reference to FIG. 4, it can observed that there are a pair of pH indicators 22 and 24 which are applied to the lower end of the shank 12. In this case, the pH indicators can be initially liquid and impregnated into the lower end of the shank 12. Otherwise, they could be applied and retained on the lower end of the shank by any conventional means. For that matter, small strips of paper containing an impregnated pH indicator could be applied to the lower end of the shank 12.

A dentist or technician can take a small piece of paper, roll it into a thin small diameter roll having a very small diameter lower end. The roll of paper can then be dipped into a liquid pH indicator to impregnate the paper roll at least at the tip. Time must be allotted to any liquid carrier on the paper roll to dry.

Many well known dyes can be used as a pH indicator. Some of these dyes provide a greater sensitivity if optical pH measurements are to be made. However, in most cases, it is not necessary to measure the pH, but only to determine if there is any pH above or below 7.0. However, if quantitative measurement is desired, it would be necessary to measure the pH and match the indicators $pK_3$ to the pH. Nevertheless, for the purposes of the present invention, quantitative measurements are not described.

Some of the specific pH indicators which can be used include, for example, those base testing pH indicators, such as phenolphtalein, litmus and phenol red. There are also a variety of know basic pH testing indicators which can be used include, for example, bromothymol blue or methyl red.

It is also possible use other pH indicators which have differing pH color indicator ranges. For example, litmus paper which will render a red color in an acid pH range and a blue color in a base pH range. Bromocresol green will exhibit different colors for differing pH ranges. The same holds true or methyl orange and thymol blue. For the present invention, a number of pH indicators could also be applied to either a rolled up piece of paper or otherwise any other type of implement in accordance with the invention.

The amount of the pH indicator which is applied is not critical in accordance with the invention, although it must be at least sufficient to provide a clear color change to enable the dentist or other dental practitioner to determine whether or not moisture is present by a color change. It may also be used to provide a very rough indication as to whether or not the moisture which may be present is acidic or basic and thereby provide some aid in determining general groups of bacterial growth which may be present.

The method of the present invention can also be used in a very low cost manner by allowing a dental practitioner to roll up a piece of paper with a lower pointed end. Again, drying time for evaporation of any liquid carrier must be allowed. The practitioner would then impregnate that piece of paper with a pH indicator. For purposes of the present invention, two different moisture testing implements can used and can be provided in pairs. Thus, one implement may have an acidic pH indicator and another in the pair may have a basic pH indicator.

Thus, there has been illustrated and described a unique and novel root canal testing and canal drying and which thereby fulfills all of the objects and advantages which have been sought. It should be understood that many changes, modifications, variations and other uses and applications which will become apparent to those skilled in the art after considering the specification and the accompanying drawings. Therefore, any and all such changes, modifications, variations and other uses and applications which do not depart from the spirit and scope of the invention are deemed to be covered by the invention.

Having thus described the invention, what we desire to claim and secure by Letters Patent is:

1. A method for detecting whether moisture is present in a root canal of a tooth, said method comprising:
    a) inserting an implement containing a pH indicator into the root canal of a tooth; and
    b) withdrawing the implement from the canal of the tooth and determining whether the pH indicator has changed color which thereby provides indication of the presence of moisture.

2. The method of claim 1 further characterized in that the implement comprises an elongate paper roll having a lower pointed end thereof with the pH indicator in proximity to that lower pointed end.

3. The method of claim 1 further characterized in that the implement has a positive pH indicator and a negative pH indicator and the method therefore comprises determining whether any moisture that may be present has a negative or a positive pH component.

4. The method of claim 1 further characterized in that said method comprises rolling a piece of paper to a sharp point and applying at least one pH indicator in proximity to that sharp point of the implement.

5. The method of claim 1 further characterized in that said pH indicator is phenolpthalein.

6. The method of claim 1 further characterized in that said pH indicator is litmus.

7. An implement for determining whether or not moisture is present in a root canal of a tooth and whether that moisture may have a certain pH associated therewith, said device comprising:
    a) an elongate rod like member having an enlarged upper end for engagement by the fingers of a user;
    b) said elongate rod like member being comprised of a relatively yieldable and bendable material to conform to the shape of a canal of a tooth and which still has sufficient integrity and rigidity to allow the member to be properly inserted in the root canal of a tooth;
    c) a relatively sharp pointed tip at the lower end of said rod like member; and
    d) a pH indicator on said rod like member adjacent the lower end thereof for indicating the presence of moisture in a root canal of a tooth when the implement in inserted therein.

8. The implement of claim 7 further characterized in that said implement is a rolled piece of paper.

9. The implement of claim 7 further characterized in that the implement has a tapered lower end.

10. The implement of claim 7 further characterized in that a pair of pH indicators are provided on the lower end of the implement in proximity to the tip thereof.

* * * * *